US011324897B2

(12) United States Patent
Charlebois et al.

(10) Patent No.: US 11,324,897 B2
(45) Date of Patent: May 10, 2022

(54) INTRAOSSEOUS INJECTION DEVICE

(71) Applicant: PYNG MEDICAL CORP., Richmond (CA)

(72) Inventors: Paul Charlebois, Victoria (CA); Michael Lubben, Victoria (CA); Gregory Vincent Browne, Vancouver (CA); Christopher Grant Denny; Nicole Ranger, Vancouver (CA)

(73) Assignee: PYNG MEDICAL CORP., Richmond (CA)

( * ) Notice: Subject to any disclaimer, the term of this patent is extended or adjusted under 35 U.S.C. 154(b) by 51 days.

(21) Appl. No.: 15/755,948

(22) PCT Filed: Aug. 31, 2016

(86) PCT No.: PCT/CA2016/051033
§ 371 (c)(1),
(2) Date: Feb. 27, 2018

(87) PCT Pub. No.: WO2017/035653
PCT Pub. Date: Mar. 9, 2017

(65) Prior Publication Data
US 2018/0236182 A1 Aug. 23, 2018

Related U.S. Application Data

(60) Provisional application No. 62/212,421, filed on Aug. 31, 2015.

(51) Int. Cl.
*A61M 5/00* (2006.01)
*A61M 5/46* (2006.01)
(Continued)

(52) U.S. Cl.
CPC ............ *A61M 5/46* (2013.01); *A61B 17/3472* (2013.01); *A61M 5/00* (2013.01); *A61M 5/2033* (2013.01);
(Continued)

(58) Field of Classification Search
CPC .... A61M 5/46; A61M 5/2033; A61M 5/2466; A61M 5/31501; A61M 5/329;
(Continued)

(56) References Cited

U.S. PATENT DOCUMENTS 5,176,645 A * 1/1993 Guerrero ............... A61M 5/204
604/143
5,868,711 A 2/1999 Kramer et al.
(Continued)

FOREIGN PATENT DOCUMENTS

CA 2759585 A1 5/2012
JP 6-508773 A 10/1994
(Continued)

OTHER PUBLICATIONS

Official Action from the Japan Patent Office dated Nov. 26, 2020 for Patent Application No. 2019-233973.

*Primary Examiner* — Rebecca E Eisenberg
*Assistant Examiner* — Tania Ismail
(74) *Attorney, Agent, or Firm* — BakerHostetler

(57) ABSTRACT

A device for intraosseous injection is provided which can accurately, quickly, and safely introduce desired fluid into a patient's bone marrow. The intraosseous injector includes a housing, a container located within the housing, a hollow needle, and a valve. The intraosseous injector may further include a release mechanism comprising a bone probe needle and a movable release member. The intraosseous injector may include a depth limiter mechanism operable to limit a depth of penetration of the needle relative to a surface
(Continued)

of a bone. A method for intraosseous injection is also provided.

30 Claims, 9 Drawing Sheets

(51) Int. Cl.
*A61B 17/34* (2006.01)
*A61M 5/28* (2006.01)
*A61M 5/20* (2006.01)
*A61M 5/24* (2006.01)
*A61M 5/315* (2006.01)
*A61M 5/42* (2006.01)
*A61M 5/32* (2006.01)

(52) U.S. Cl.
CPC ........ *A61M 5/2053* (2013.01); *A61M 5/2466* (2013.01); *A61M 5/288* (2013.01); *A61M 5/31501* (2013.01); *A61M 5/427* (2013.01); *A61M 5/2455* (2013.01); *A61M 5/329* (2013.01); *A61M 2005/2474* (2013.01); *A61M 2205/583* (2013.01); *A61M 2210/02* (2013.01)

(58) Field of Classification Search
CPC ........ A61M 5/2455; A61M 2005/2474; A61M 2205/583; A61M 5/2053; A61B 17/3472
See application file for complete search history.

(56) References Cited

U.S. PATENT DOCUMENTS

| | | | |
|---|---|---|---|
| 6,761,726 | B1 | 7/2004 | Findlay et al. |
| 2002/0007142 | A1* | 1/2002 | Hjertman ................ A61M 5/30 |
| | | | 604/38 |
| 2005/0148940 | A1 | 7/2005 | Miller |
| 2005/0261693 | A1 | 11/2005 | Miller et al. |
| 2010/0298830 | A1 | 11/2010 | Browne et al. |
| 2010/0298831 | A1 | 11/2010 | Browne et al. |
| 2012/0078172 | A1 | 3/2012 | Bendek et al. |
| 2012/0107783 | A1* | 5/2012 | Julian ................ A61M 5/2033 |
| | | | 434/262 |
| 2013/0211330 | A1 | 8/2013 | Pedersen et al. |
| 2013/0226080 | A1* | 8/2013 | Davies ................ A61M 5/2448 |
| | | | 604/89 |
| 2015/0320936 | A1* | 11/2015 | Dunne ................ A61M 5/288 |
| | | | 604/199 |

FOREIGN PATENT DOCUMENTS

| | | |
|---|---|---|
| JP | 2013534164 A | 9/2013 |
| WO | 0019735 A1 | 4/2000 |
| WO | 2009070896 A1 | 6/2009 |
| WO | 2013/190941 A1 | 12/2013 |

* cited by examiner

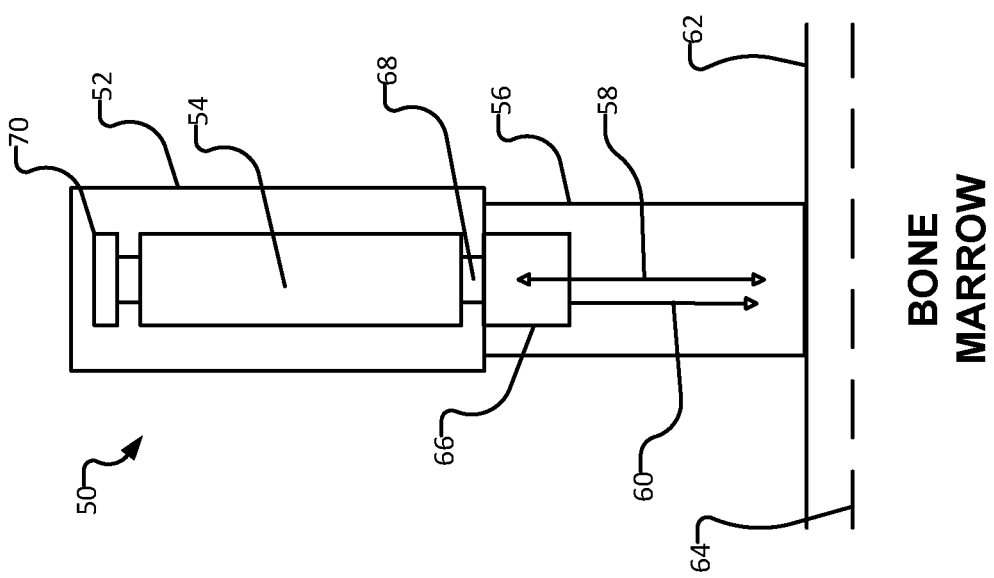
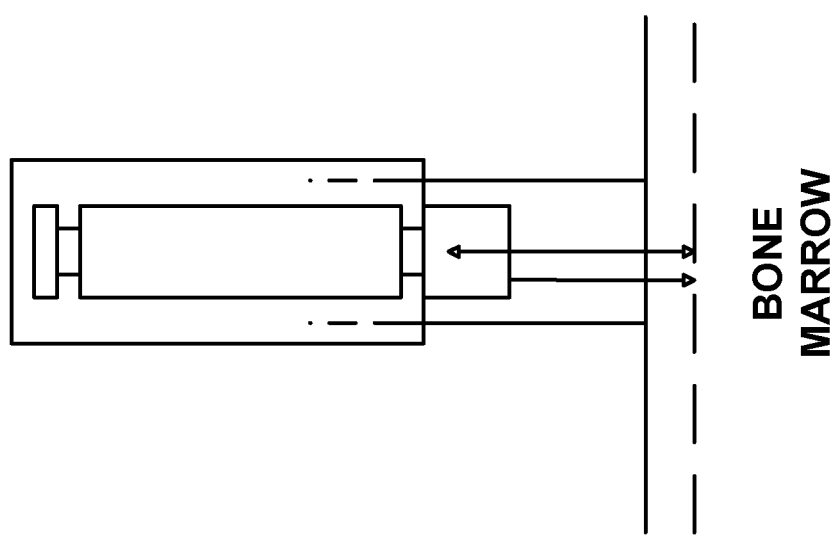
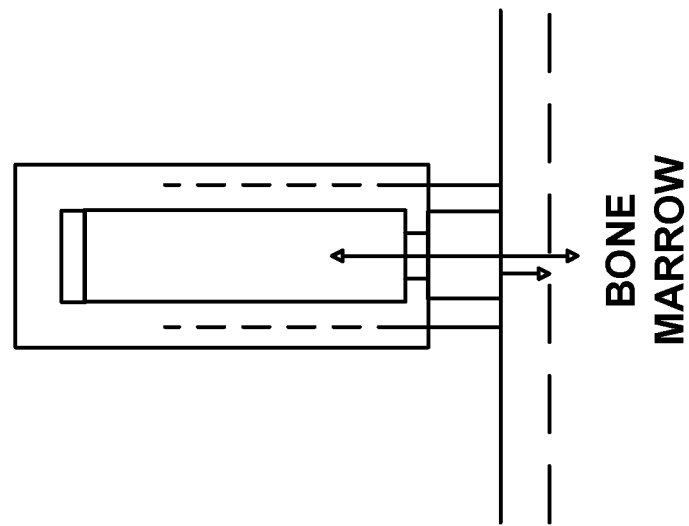

INTRAOSSEOUS INJECTION DEVICE

CROSS-REFERENCE TO RELATED APPLICATIONS

This application claims priority from U.S. Application No. 62/212421 filed 31 Aug. 2015. For purposes of the United States, this application claims the benefit under 35 U.S.C. § 119 of U.S. Application No. 62/212421 filed 31 Aug. 2015 and entitled INTRAOSSEOUS INJECTION DEVICE which is hereby incorporated herein by reference for all purposes.

TECHNICAL FIELD

This invention relates to intraosseous injection devices, and in particular to injectors suitable for delivery of drugs and other fluids.

BACKGROUND

It is well known that in emergency situations, introducing certain fluids, such as medicines, antidotes, or other drugs, into a patient's system can be lifesaving. Injecting a fluid directly into a patient's bone marrow ("intraosseous injection"), rather than into a muscle or vein, provides faster delivery of that fluid. There remains a need for an intraosseous injection device which can quickly and safely introduce a desired fluid into a patient's bone marrow.

BRIEF DESCRIPTION OF DRAWINGS

The accompanying drawings illustrate non-limiting example embodiments of the invention.

FIGS. 1A-1C are schematic drawings showing an example intraosseous injection device in a sequence illustrating of how the device may be used according to one embodiment of the invention.

DETAILED DESCRIPTION

Figure 1D:
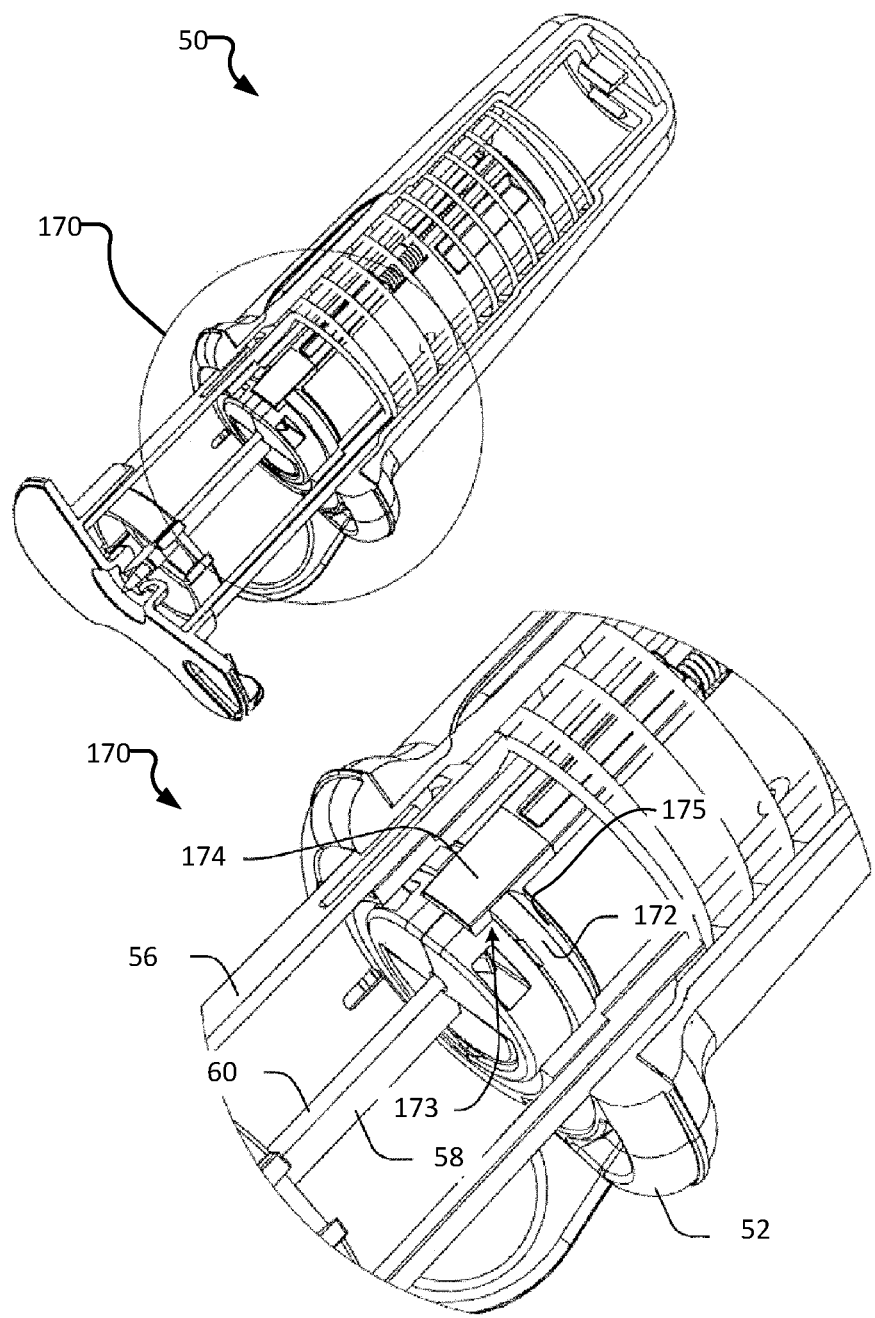
FIG. 1D is a schematic view of a release mechanism, as used in some embodiments of the invention.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

A number of directional conventions are employed in this specification to help clarify their meaning, as follows: "upward", "upwardly", "upwardmost", "top" and similar words refer to a direction extending towards the top of the page; "downward", "downwardly", "downwardmost", "bottom", "lower", "lowermost" and similar words refer to a direction extending towards the bottom of the page. These conventions pertain only to the drawings, and do not necessarily reflect how embodiments of the invention may be used in practice.

The invention relates to intraosseous injection devices. This description describes various features that such devices may have. These features may be combined in different combinations to yield various embodiments of the invention. Such features may also be applied individually or in combination with existing devices. The description describes, among others:

Features relating to delivering fluid into a bone-penetrating needle;

Features related to pressurizing fluids for intraosseous delivery;

Features related to adjusting the volume of fluid to be delivered by an injector;

Features for indicating when an injection of fluid is complete.

A range of options is provided for each of these groups of features. Any of the options for delivering fluid into a bone-penetrating needle may be used alone or combined with any of the options for pressurizing fluids. Any of these embodiments may optionally be combined with an option for adjusting the volume of fluid to be delivered. The features related to pressurizing fluids for intraosseous delivery and the features related to adjusting the volume of fluid to be delivered by an injector may also be applied individually or in combination with one another. Any described option for indicating when an injection of fluid is complete may be applied individually or in combination with any of the above.

In accordance with one aspect of the invention, an injection device is operative to establish a fluid connection between a compartment containing a fluid, such as a medicine, antidote, or other drug and the bone marrow of a patient. Some embodiments of the invention are well adapted for use in emergency and mass casualty situations, where patients are in immediate need of the fluid contained in the compartment. One aspect of the invention provides injection devices wherein one end of a stylet needle pierces a septum or otherwise establishes a fluid connection to a source of fluid and the other end of the stylet needle penetrates a patient's sternum in order to put the bone marrow of the patient in contact with the fluid.

FIGS. 1A-1C (collectively, along with FIG. 1D, "FIG. 1") show schematically an intraosseous injection device 50 according to one example embodiment of the invention. The sequence of FIGS. 1A to 1C illustrates how device 50 may be used in practice. For clarity, some elements in FIGS. 1B and 1C that are the same as elements shown in FIG. 1A are not labelled.

Example injection device 50 comprises a handle 52 housing a compartment 54. Compartment 54 may be pre-loaded with a fluid, such as a medicine, drug, serum, antidote, infusion, electrolyte solution, or other fluid to be injected into a patient. In some embodiments, the fluid may be used in an emergency situation, for example to aid a patient who has gone into cardiac arrest, to help mitigate the effects of a toxin in a patient's system, to help mitigate an allergic reaction, to help in treatment of severe trauma, to help in treatment of blood loss or the like. In some embodiments the fluid comprises one or more of: epinephrine, antidotes, heart medications, and medications to treat one or more of: blood loss, infections, hypotension, organophosphate poisoning, burns, trauma, pain and seizures. In some embodiments the amount of fluid in compartment 54 is in the range of about 1 millilitre (mL) to about 15 mL. For example compartment 54 may contain 3 mL or 5 mL of fluid in some embodiments.

In the following description the direction toward a patient may be called the "proximal" direction, while the opposite direction away from the patent may be called the "distal" direction. Proximal and distal may also be used to describe directions and locations of parts of an injection device. The direction extending from handle 52 towards needle housing 56 is the "proximal" direction, while the opposite direction is the "distal" direction.

Device 50 may be used by positioning the device at a suitable location over a bone of a patient into which it is desired to inject a fluid. For example, the bone may be a sternum, tibia or other intraosseous injection site. Handle 52 may then be pushed toward the patient (i.e. in the proximal direction) to drive a needle 58 into the bone marrow of the patient. A depth control mechanism or "depth limiter" stops needle 58 from being driven deeper into the patient when needle 58 has reached a desired depth below a surface of the bone. Operation of the depth limiter may, for example, uncouple needle 58 from handle 52 such that further proximal motion of handle 52 does not cause needle 58 to advance. Operation of the depth limiter may result in the establishment of a fluid connection between the interior of compartment 54 and needle 58.

In the illustrated embodiment, the depth to which needle 58 is driven past the surface of the patient's bone is determined by a depth limiter mechanism that includes one or more probes 60. Probe 60 is stopped at the surface of the patient's bone. The depth limiter may be triggered when the tip of needle 58 projects a predetermined desired distance past the tip of probe 60 in the distal direction.

Once the depth limiter has been triggered to stop needle 58 at the desired depth, needle 58 may be uncoupled from handle 52. In some embodiments, continued motion of handle 52 or a portion thereof in the proximal direction after the depth limiter has been triggered establishes a fluid connection between the interior of compartment 54 and hollow needle 58. Compartment 54 may be pressurized so that its contents are urged to flow through needle 58 into the patient once the fluid connection has been established.

In the illustrated embodiment, continued motion of handle 52 in the proximal direction after the depth limiter has been triggered carries compartment 54 toward the distal end of needle 58. This relative motion may open a fluid connection between the interior of compartment 54 and a passage interior to needle 58. For example, the relative motion between compartment 54 and needle 58 may cause the distal end of needle 58 to enter compartment 54, thereby allowing the fluid in compartment 54 to flow through needle 58 and into the patient's bone marrow. Once the fluid has been injected, injection device 50 may be removed from the patient.

In some embodiments, a sharp distal end of needle 58 may pierce septum 68 which seals compartment 54, allowing needle 58 to enter compartment 54 while maintaining a seal around needle 58. This facilitates the flow of the fluid in compartment 54 into the patient. In other example embodiments, relative motion of needle 58 relative to handle 52 and/or compartment 54 opens a valve, breaks a sealed compartment 54, or otherwise establishes a fluid connection which allows the fluid contents of compartment 54 to flow into the patient through needle 58.

In the illustrated embodiment apparatus 50 includes a needle housing 56 which is retractable into handle 52. A base on the proximal end of needle housing 56 may assist in orienting device 50 at a suitable angle to the patient (typically with needle 58 perpendicular to the patient's bone) and/or in positioning device 50 at a desired injection site.

In the example device 50 of FIG. 1, needle 58 is supported by a carriage mechanism 66. The depth limiter includes a coupling that initially couples carriage mechanism 66 to handle 52, such that when handle 52 is moved proximally carriage mechanism 66 is also moved proximally.

Needle 58 and probe 60 are also coupled to carriage mechanism 66. While the depth limiter keeps carriage mechanism 66 coupled to handle 52 compartment 54 is kept spaced apart from the distal end of needle 58. When the depth limiter detects that needle 58 is at the desired depth, the depth limiter releases the coupling of carriage mechanism 66 to handle 52. This allows carriage mechanism 66 and compartment 54 to move toward one another.

FIGS. 1A to 1C illustrate a sequence of steps in the operation of device 50. Injection device 50 may be placed by a user on a patient's skin 62 above a target bone 64, as shown in FIG. 1A. As described above, handle 52 is initially coupled to carriage mechanism 66.

A user may then begin to press handle 52 in the proximal direction (downwards in FIG. 1A) toward the patient, as shown in FIG. 1B. As this occurs, needle housing 56 is telescoped into handle 52 as denoted by the dashed lines in FIGS. 1B and 1C. As carriage mechanism 66 is carried correspondingly downward, needle 58 and probe 60 are caused to extend past the proximal end of needle housing 56 through the patient's skin 62 to contact the surface of bone 64. As can be seen in FIG. 1B, up to this point there is no fluid connection between the interior of needle 58 and compartment 54. The distal end of needle 58 remains spaced apart from compartment 54.

Probe 60 is designed to penetrate only the patient's skin 62 and underlying tissue; that is, probe 60 is designed to come to rest at the surface of bone 64. The tip of probe 60 thereby provides a direct measure of the location of the bone surface. The bone surface sets a reference point for the depth of the bone marrow. There is relatively little variation in the thickness of the surface layers of most patients' bones. The thickness of the surface layer of the sternum tends to be quite consistent. There is more variation in the thickness of the surface layers of other bones, such as bones in the extremities. This variation is generally small enough that a penetration depth can be selected that will reliably introduce needle 58 into the bone marrow of a patient. By contrast the variations in the thickness of tissue above the bone can be quite significant. For example, the thickness of tissue above a patient's sternum may range from approximately 4 millimetres (mm) to approximately 25 mm, depending on the patient.

As shown in FIG. 1C, as the user continues to push handle 52 proximally towards the patient, the proximal end of needle 58 penetrates bone 64 and contacts the underlying bone marrow. When needle 58 reaches the depth of the bone marrow, as defined relative to the rest location of probe 60, further advance of needle 58 is stopped by the depth limiter. The depth limiter may, for example, be triggered by needle 58 projecting a threshold distance (e.g. a few mm) past the tip of probe 60. In some embodiments needle 58 is positioned such that its tip is in the range of 4 mm to 8 mm (e.g. 6 mm) below the surface of the bone when the depth limiter is triggered.

Non-limiting examples of mechanisms that may be used to provide a depth limiter are described in PCT application No. CA96/00873, filed 23 Dec. 1995, and U.S. Pat. No. 6,761,726, filed 2 Mar. 2000, and PCT/CA2008/002146 published as WO 2009/070896 all of which are hereby incorporated herein by reference.

In the illustrated embodiment the depth limiter functions to uncouple carriage mechanism 66 from handle 52 once needle 58 reaches the correct depth below the surface of the patient's bone. This uncoupling allows relative motion between needle 58, which remains coupled to carriage mechanism 66, and compartment 54. The user may continue to push down on handle 52 to cause the distal end of needle 58 to penetrate septum 68 and enter compartment 54.

Septum 68 is configured such that the force required from a user to cause needle 58 to penetrate septum 68 is less than the force required to push needle 58 further into the patient. This ensures that needle 58 stays at the appropriate depth in the bone marrow as septum 68 is penetrated.

In the example embodiment of FIG. 1C, carriage mechanism 66 contacts skin 62 when handle 52 is fully depressed and needle 58 is in its final position. This is for illustrative purposes only. For patients with thinner overlying tissues and/or other embodiments, carriage mechanism 66 may not contact skin 62 when in its final position. In other embodiments a base may be provided. In such embodiments handle 52 and/or carriage mechanism 66 may contact the base when handle 52 is fully depressed and needle 58 is in its final position.

Once septum 68 is penetrated by the distal end of needle 58, the fluid in compartment 54 may then be forced out of compartment 54. The fluid in compartment 54 may be pressurized such that it tends to flow out of compartment 54 when septum 68 is pierced.

In some embodiments, fluid may be pressurized by a pressurization mechanism 70 prior to use of injection device 50. In some embodiments, pressurization mechanism 70 operates independently of the force the user applies to handle 52. In other embodiments some of the force exerted by a user as device 50 is used is applied to pressurize compartment 64. In other embodiments, the interior of compartment 54 may be pressurized at the time compartment 54 is filled.

Where a pressurization mechanism 70 is provided the pressurization mechanism may be disabled until just prior to injection. This reduces the likelihood that the fluid will leak out of compartment 54 prior to injection. In an example embodiment the pressurization mechanism comprises a spring. The spring may be held back from advancing to pressurize the contents of compartment 54 by a removable stop such as a pin, catch or the like. A user may operate the stop to allow the spring to pressurize the contents of compartment 54 prior to use of device 50. In an example embodiment the spring is arranged such that release of energy stored in the spring reduces a volume of compartment 54. For example, the spring may be arranged to urge a plunger to advance along compartment 54 or to deform a chamber 54 that is deformable (e.g. bellows-shaped).

In some embodiments a mechanism is provided to adjust the amount of fluid injected. For example, there are circumstances where a dose of an active ingredient sufficient for a large man may be too large to give a small woman or child. An adjustment mechanism can allow a user to tailor the dose to be delivered to the needs of a specific patient.

The adjustment mechanism may take a wide variety of forms. In some embodiments the travel of a plunger that forces fluid out of compartment 54 or the travel of a mechanism that actuates the plunger is controlled. In some embodiments an adjustable stop limits the advance of a plunger that forces fluid out of compartment 54. Position of the stop may be set by adjusting a position of a knob, dial, pin, lever or the like.

For example, a user may set the stop to inject one of: a full dose, or one of two or three fractional doses (e.g. half dose or ⅓ dose or ¼ dose) in some embodiments. In other embodiments the position of the stop may be continuously variable over some range. In other embodiments compartment 54 is one of a plurality of compartments 54 each equipped with a pressurization mechanism. A user may activate pressurization mechanisms for one, two or more of the plurality of compartments to set the amount of fluid delivered to a patient. In some embodiments different ones of the compartments carry different fluids. In some embodiments the compartment comprises a removable cartridge. Cartridges containing different amounts of fluid and/or different amounts of an active ingredient in a fluid. A user may select a cartridge containing an amount of an active ingredient suitable for a specific patient.

After device 50 has been deployed as described above, the user of injection device 50 may hold injection device 50 against the patient for a period of time sufficient to allow the fluid to be fully injected. After the fluid from compartment 54 has been fully injected, injection device 50 may be removed from the patient.

Injection device 50 may comprise an indicator (not shown in FIGS. 1A to 1C) which indicates when the fluid has been fully injected. The example embodiment of FIG. 1C comprises a pressurization mechanism that includes a plunger biased to compress fluid in compartment 54. The plunger advances as fluid is ejected from compartment 54. Motion of such a plunger may be the basis for an indicator mechanism. For example, device 50 may include a window through which a portion of the plunger or a member connected to be moved by the plunger may be viewed in order to indicate to a user when the injection is complete.

A control may optionally be provided to set a rate at which fluid is delivered into a patient. For example, in certain cases it may be desirable to infuse the fluid into the patient more slowly and in other cases it may be desirable to deliver the fluid to the patient more quickly. The rate control may, for example, comprise an adjustable valve between the compartment and the needle, a device that regulates advance of a plunger of a pressurization mechanism or the like. In an example embodiment a rate control comprises a button that allows the plunger of a pressurization mechanism to advance incrementally each time it is pressed. A control may be provided to selectively enable or disable the rate control mechanism.

As the user pulls handle 52 distally, needle 58 and probe 60 are pulled out of the patient. At the same time, needle housing 160 may extend to cover the proximal end of needle 58. Carriage mechanism 66 may be prevented from moving back to its original position in handle 52 by a ratchet (not shown).

The principles of operation of injection device 50 may be applied in a wide variety of constructions. Some non-limiting examples of such constructions are illustrated in FIGS. 2-8.

Figure 4:
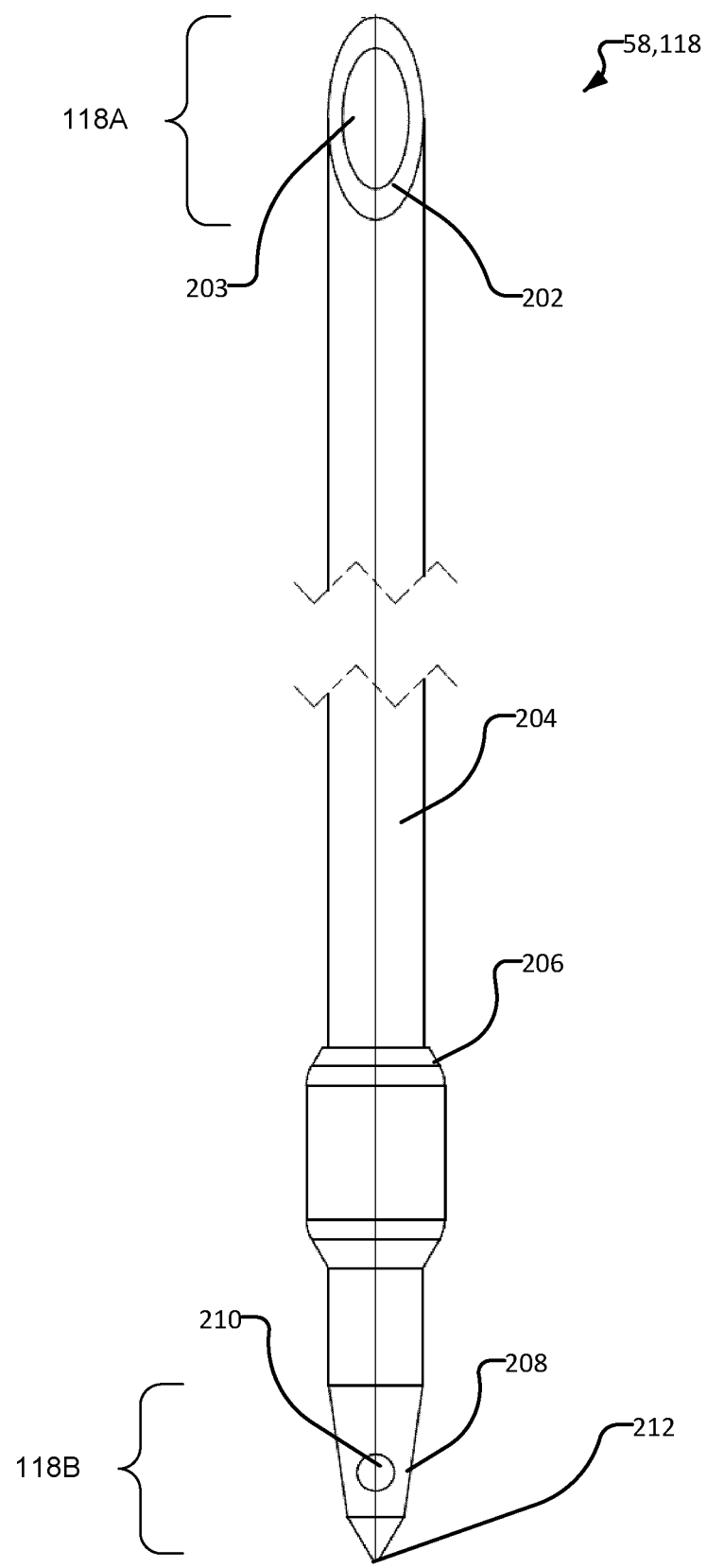
FIG. 4 is a schematic view of the stylet needle used in an intraosseous injection device, according to one embodiment of the invention.

As can be seen in the example embodiment of FIG. 4, the proximal end of needle 58 may comprise a sharp end 212 and one or more injection ports 210, located on the side of needle 58 distally to sharp end 212. The one or more injection ports 210 communicate with a hollow bore 203 extending through needle 58, through which the fluid may flow. This construction tends to avoid plugging of ports 210 as needle 58 is driven into the patient's bone. A needle 58 as shown in FIG. 4 may be applied in any of the embodiments described herein.

In some embodiments the distal end of needle 58 is configured to make a fluid connection with the contents of compartment 54. In some such embodiments needle 58 has opposing sharp ends. In such embodiments a proximal end of needle 58 is designed to penetrate the patient's bone 64. A distal end of needle 58 may be designed to pierce a septum 68. In other such embodiments the distal end of needle 54 may be configured to open a valve, break a vial or otherwise release fluid to be injected through needle 58.

As described above, In some embodiments, the depth limiter comprises a release mechanism comprising a split ring and a sliding block. An example of such a release mechanism 170 is shown in FIG. 1D. In this embodiment, split ring 172 sits in a groove 175 in handle 52 and has a thickness that projects radially inwardly to engage carriage mechanism 66. Ends of split ring 172 define a gap 173 that is initially filled by a sliding block 174, which is coupled to probe 60.

Probe 60 is biased in a proximal direction, for example by a spring. The bias force on probe 60 is sufficient to allow probe 60 to be driven through a patient's skin and superficial tissues but is not sufficient to drive probe 60 significantly into a patient's bone 64.

In this configuration, split ring 172 couples handle 52 to carriage mechanism 66. The distal side of groove 175 is tapered such that split ring 172 is compressed radially as handle 52 pushes split ring 172 in the proximal direction. Sliding block 174 prevents split ring 172 from collapsing radially inwardly.

When probe 60 comes to rest at the surface of bone 64, continued downward motion of handle 52 causes sliding block 174 to be displaced relative to gap 173. Eventually sliding block 174 leaves gap 173. Split ring 172 then collapses radially inwardly out of groove 175. This releases carriage mechanism 66 from being driven by handle 52 and leaves needle 58 inserted to the depth that it was driven to before carriage mechanism 66 was released.

Figure 2:
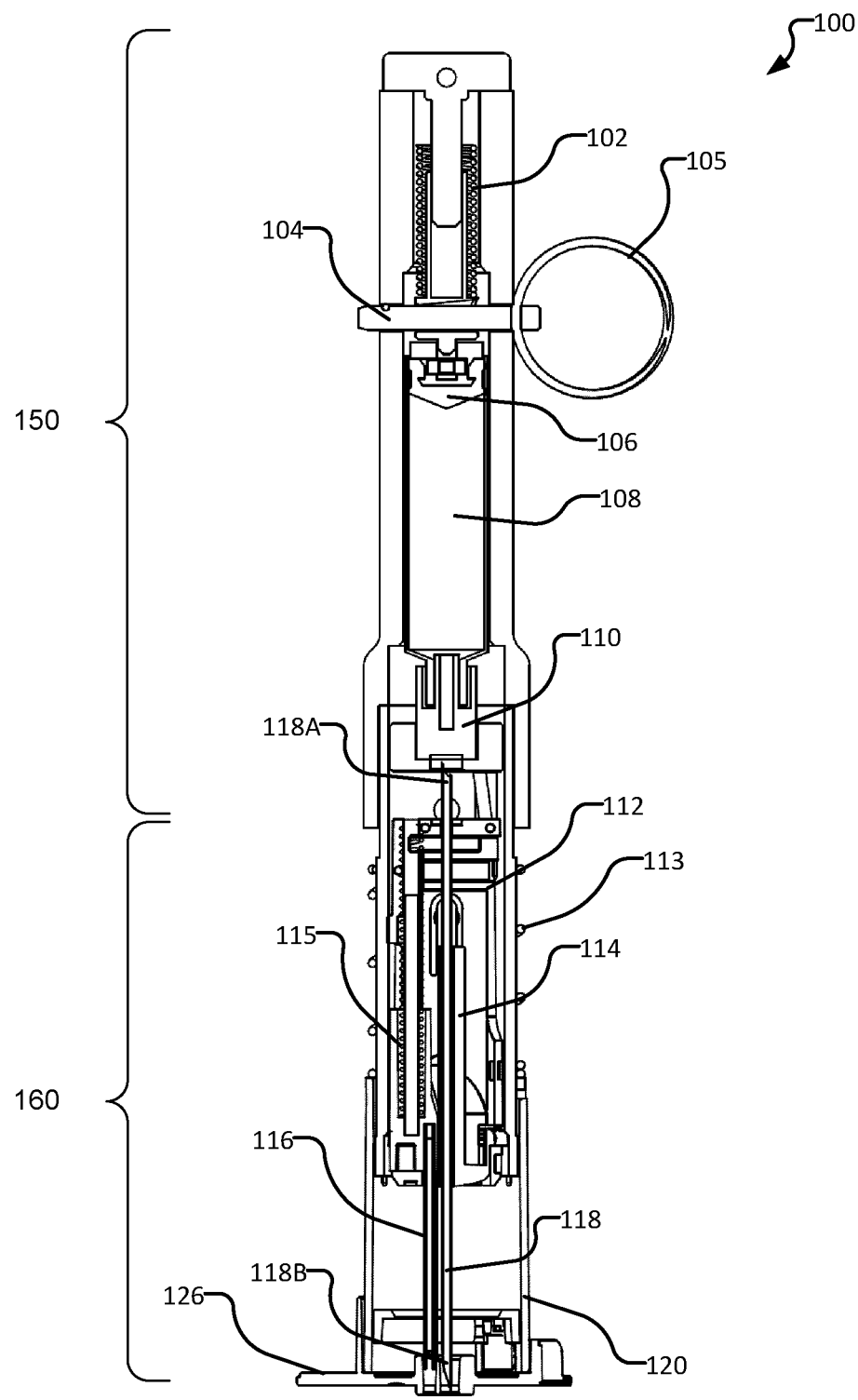
FIG. 2 is a detailed schematic cross-sectional side view of an intraosseous injection device according to an example embodiment of the invention.

FIG. 2 is a detailed side view of an intraosseous injection device 100 according to one example embodiment. An outer grip may be provided. The outer grip is omitted from FIG. 2 for clarity.

As viewed externally, injection device 100 comprises handle 150 and needle housing 160. Handle 150 and needle housing 160 have generally tubular bodies. Needle housing 160 may telescope into handle 150.

Injection device 100 comprises a pressurization mechanism which is energized by a compression spring 102. Pin 104 prevents compression spring 102 from contacting compartment 108 when injection device 100 is not in use. When injection device 100 needs to be used, pin 104 may be removed by pulling on pin ring 105. This allows compression spring 102 to extend and pressurize the contents of compartment 108.

Spring 102 may axially compress compartment 108. For example, one end of compartment 108 may comprise a membrane which flexes and compresses the fluid in compartment 108 when contacted by spring 102. In other embodiments, one top end of compartment 108 may comprise a plunger 106, which compresses the fluid inside compartment 108 when advanced by spring 102.

Prior to using device 100 the user removes actuation pin 104, by pulling on pin ring 105, to allow compression spring 102 to advance plunger 106 to pressurize the contents of compartment 108.

In order to inject the fluid contained in compartment 108 into a patient's bone marrow, a user first places the foot 126 on an appropriate spot, or "injection location", on the patient's body. Foot 126 helps to stabilize injection device 100 during injection. Foot 126 may also comprise features which aid a user in locating the appropriate spot for injection.

The injection location may be, for example, in the chest, thigh, or other area which provides easy access to a patient's bone marrow. The bone corresponding to this location (for example, the sternum, tibia, or femur) may be called the "target bone". In some embodiments, the patient's sternal notch is aligned with indicia on foot 126 (e.g. a notch in the edge of foot 126) to align needle 58 over a target location on the patient's sternum.

With device 100 properly positioned and pin 104 removed, the user may then begin to press handle 150 in the proximal direction toward the patient. As shown in FIG. 1, handle 150 is slidably movable relative to needle housing 160, such that needle housing 160 may telescope into handle 150 as handle 150 is moved.

The proximal motion of handle 150 is resisted by recoil spring 113, which biases handle 150 away from needle housing 160. A user must provide enough proximal force to overcome the resistance from recoil spring 113 to cause handle 150 to move.

As described above, handle 150 is initially coupled to carriage mechanism 112, which is in turn coupled to needle 118. Carriage mechanism 112 may remain coupled to handle 150 until stylet needle 118 has penetrated the patient's bone to a desired depth, at which time carriage mechanism 112 may be uncoupled from handle 150.

In the illustrated injection device 100, release of carriage 112 is triggered by a relative motion of one or more bone probes 116 and needle 118. Spring 115 biases the one or more bone probes 116 in a proximal direction. The one or more bone probes 116 may comprise needles which are designed to extend past foot 126 to pierce the patient's skin and tissue. Probe spring 115 does not provide enough force to allow the one or more bone probes 116 to penetrate significantly into the patient's bone. Thus, as described above, the one or more bone probes 116 set a reference point for the depth of the patient's bone marrow.

Devices as described herein may include any suitable number of bone probes 116. Where there are two or more bone probes 116 the bone probes 116 may be arranged in any suitable constellation around needle 118. For example, bone probes 116 may be arranged in a straight line, a triangle, a square, a rectangle, a circle, a semicircle, etc. around or adjacent to bone-piercing end 118B of needle 118. In some embodiments, the one or more bone probes 116 may work together with foot 126 to stabilize injection device 100 while stylet needle 118 is extended.

As the user continues to push on handle 150, bone-piercing end 118B of stylet needle 118 extends proximally out of needle housing 160 past the one or more bone probes 116 and penetrates the patient's bone before coming to rest in the underlying bone marrow. Bone-piercing end 118B may be stopped by a depth limiter, as described above.

Injection device 100 may also comprise an anti-buckle mechanism 114 to prevent stylet needle 118 from bending or breaking under the significant forces placed on it while penetrating the sternum (or other target bone). The anti-buckle mechanism may, for example comprise a member or members that support needle 118. In some embodiments the anti-buckle mechanism comprises one or more rings or bores through which needle 118 passes.

In some embodiments, stylet needle 118 may extend through the patient's skin and tissue and reach the surface of the patient's bone approximately simultaneously with the one or more bone probes 116. Bone-piercing end 118B may then penetrate the sternum or other target bone while the one or more bone probes 116 remain stationary on the surface of the target bone.

Once bone-piercing end 118B reaches the appropriate depth, a release mechanism may be activated to release carriage mechanism 112 from handle 150. The release mechanism may, for example comprise a release mechanism like release mechanism 170 of FIG. 1D. Other release mechanisms are possible. For example U.S. Pat. No. 5,817,052 and the other references listed above describe example release mechanisms.

In some embodiments, release mechanism 170 does not release carriage mechanism 112 until stylet needle 118 has penetrated the sternum or other target bone and made contact with the patient's bone marrow. This may be achieved, for example, by designing sliding block 174 to have a sufficient longitudinal (i.e. proximal-to-distal) length, such that sliding block 174 stays in gap 173 until stylet needle 118 has fully penetrated the bone to a desired depth. Only then does split ring 172 move past sliding block 174 and collapse to release carriage mechanism 112. Carriage mechanism 112 may be released as split ring 172 collapses and disengages from handle 150. This allows stylet needle 118 to come to rest at the appropriate depth while handle 150 continues to move.

After release mechanism 170 is activated, compartment 108 may then move relative to stylet needle 118, which remains stationary. As the user continues to push handle 150 proximally, septum 110 and compartment 108 continue to move proximally as well, eventually causing septum-piercing end 118A of stylet needle 118, which remains stationary, to penetrate septum 110 and enter compartment 108.

When injection device 100 is not in use, septum 110 works with plunger 106 to seal compartment 108 and isolate the fluid inside. When pierced by septum-piercing end 118A, septum 110 allows the fluid to flow out of compartment 108 through stylet needle 118.

Once handle 150 has been fully depressed and stylet needle 118 is in its final position, the fluid in compartment 108 may be forced through stylet needle 118 by plunger 106. Plunger 106 is advanced by compression spring 102.

The amount of time required to fully inject the fluid from compartment 108 into the patient's bone marrow depends on factors such as the spring constant of compression spring 102, the volume of compartment 108 and the geometry of the fluid passages in needle 118. In some embodiments, compression spring 102 and compartment 108 are chosen such that the fluid is fully injected in less than three seconds.

Once the fluid has been fully injected injection device 100 may be removed from the patient. As the user stops pressing proximally on handle 150, recoil spring 113 pushes handle 150 upwards towards its original position. This causes similar upward motion of carriage mechanism 112, which may be coupled to handle 150 for motion in the distal direction by a ratchet or other one-way coupling.

Once stylet needle 118 and the one or more bone probes 116 have been removed from the patient, bone-piercing end 118B of stylet needle 118 and the one or more bone probes 116 may be retracted into needle cover 120 portion of needle housing 160. This prevents unwanted accidental contact with these needles.

Injection device 100 may comprise a ratchet which prevents carriage mechanism 112 from leaving handle 150 as injection device 100 is removed from the patient. This facilitates the retraction of stylet needle 118 and the one or more bone probes 116 into needle cover 120 as injection device 100 is removed from a patient.

Figure 3:
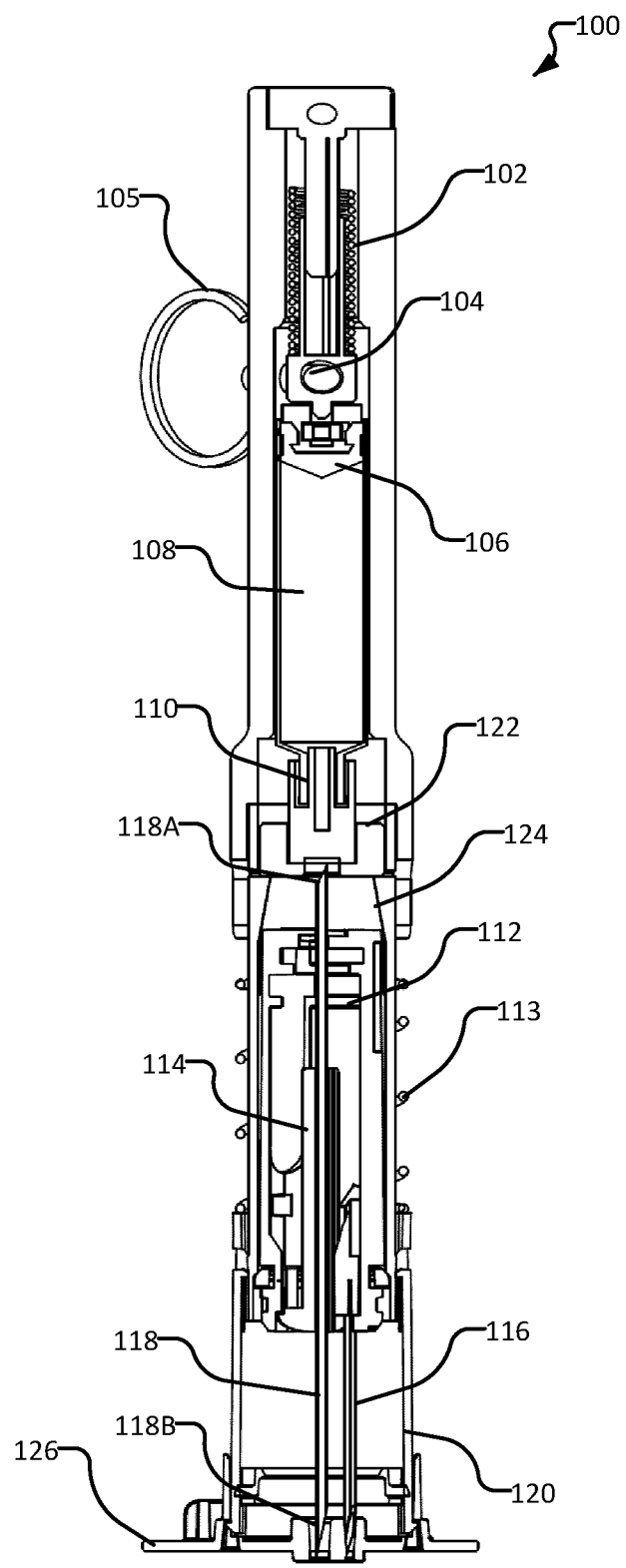
FIG. 3 is a detailed schematic cross-sectional front view of the intraosseous injection device shown in FIG. 2.

A fluid compartment 108 may be made of any suitable material or combination of materials (e.g. glass, plastic or metal compatible with the fluid to be housed). In some embodiments compartment 108 is fixed in position in the handle assembly. In other embodiments compartment 108 is movable inside the handle assembly. FIG. 3 is a front cross section view of the intraosseous injection device 100 shown in FIG. 2. Again, the outer grip is omitted for clarity. In the FIG. 3 embodiment, triggering of the depth limiter also triggers motion of container 108 relative to handle 150 in the proximal direction.

In FIG. 3, compartment 108 is supported by compartment carrier 122 and compartment carrier trigger tabs 124. Until the depth limiter is triggered, compartment 108 is held against moving proximally inside the handle assembly by tabs 124. When the depth limiter is triggered, tabs 124 move to permit compartment carrier 122 and compartment 108 to move proximally. The proximal motion of compartment 108 helps to fluidly engage needle 118 with compartment 108.

In the illustrated embodiment, after the depth limiter is triggered (thereby allowing carriage 112 to move distally relative to handle 150) trigger tabs 124 are displaced radially outwardly by carriage 112 until compartment carrier 122 is no longer held distally against the force exerted by spring 102. Spring 102 then advances compartment 108 proximally until septum 110 is pierced by end 118A of needle 118.

FIG. 4 shows an example embodiment of a stylet needle 118. In this example embodiment, stylet needle 118 comprises a beveled tip 202, bore 203, stylet body 204, a radial projection 206, stylet tip 208, injection port 210, and sharp end 212.

Beveled tip 202 at septum-piercing end 118A is designed to pierce septum 110 and enter fluid contact with the fluid in compartment 108. As can be seen in FIG. 4, an internal bore 203 in stylet needle 118 extends through beveled tip 202 to allow the fluid to flow into stylet needle 118. Bore 203 extends through the body 204 of stylet needle 118 to stylet tip 208 at bone-piercing end 118B, and culminates in injection port 210.

Stylet body 204 may be of any length, as denoted by the dashed break lines in FIG. 4, depending on the size of injection device 100. Different sizes of injection device 100 may be used in different circumstances, depending on a patient's physical or medical condition, the type of fluid to be injected, or the amount of fluid to be injected.

Radial projection 206 is an optional feature of stylet needle 118 designed to stop stylet needle 118, and bone-piercing end 118B in particular, from continuing to move once it has reached the appropriate depth into the patient's bone marrow. In some embodiments radial projection 206 is provided by a welded seam. Radial projection 206 helps to prevent over-penetration of bone-piercing end 118B. The proximal end of radial projection 206 generally comes to rest on the surface of the target bone, adjacent to the one or more bone probes 116, while stylet tip 208 extends through the target bone to allow injection port 210 to contact the patient's bone marrow. Radial projection 206 may work in conjunction with the example depth limiter described above, or may function in combination with a force-limiting coupling to handle 52 (as described for example in PCT/CA2008/002146), to limit the movement of stylet needle 118 at the appropriate depth.

Injection port 210 at bone-piercing end 118B facilitates the flow of fluid out of stylet needle 118 into the patient's bone marrow. Injection port 210 is on the side of stylet tip 208, and not directly at sharp end 212. This design prevents injection port 210 from being clogged or blocked by tissue or bone as stylet needle 118 penetrates a patient's bone so that the fluid is able to flow freely into the bone marrow.

FIG. 4 shows one injection port 210. However, other embodiments may include more than one injection port 210, positioned in various locations on stylet tip 208. In addition, injection port(s) 210 are not necessarily circular, but can be of any desired shape (e.g. oval or slit-shaped).

Figure 5:
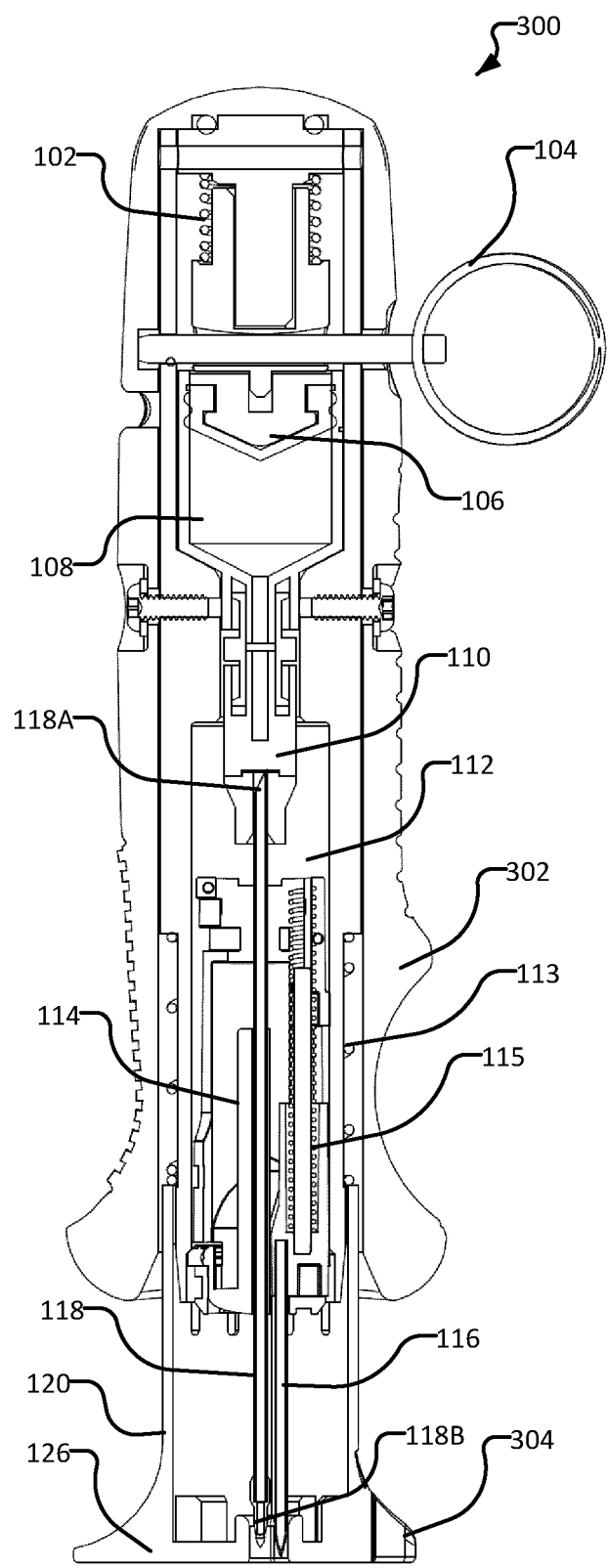
FIG. 5 is a detailed schematic cross-sectional side view of another intraosseous injection device, according to another embodiment of the invention.

FIG. 5 shows an intraosseous injection device 300, according to another example embodiment. Certain elements of injection device 300 that are the same as or similar to those shown in injection device 100 in FIGS. 2 and 3 are labelled with the same reference numbers. FIG. 5 shows grip 302 and a sternal notch locator 304.

Figure 6:
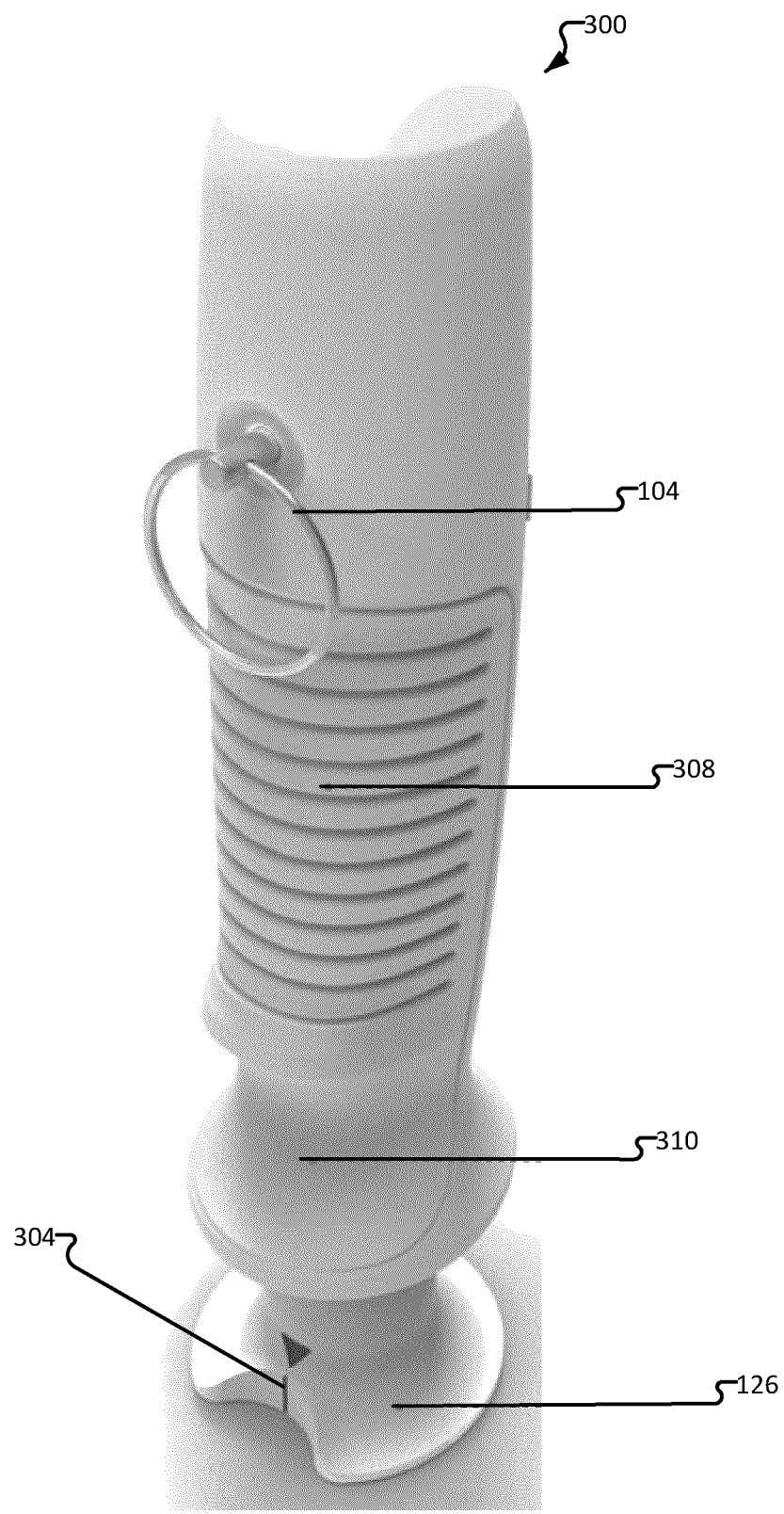
FIG. 6 is an isometric external front view of the intraosseous injection device shown in FIG. 5.
Figure 7:
FIG. 7 is an isometric external rear view of the intraosseous injection device shown in FIGS. 5 and 6.

The exterior of injection device 300 comprises grip 302. Grip 302 may aid a user in positioning and deploying injection device 300 in an emergency situation. As best shown in FIGS. 6 and 7, grip 302 may have any design, and may include some, all, or none of the following features: indicator window 306, palm grip 308, index finger rest 310, thumb rest 312, and/or the like. Grip 302 may be fused with injection device 300, or may be slidably removed to allow different grip designs to be implemented based on user preference or for specific applications.

In some embodiments, such as the one shown in FIG. 7, an indicator window 306 in grip 302 may be used to indicate when the fluid has been fully injected from compartment 108. Indicator window 306 may comprise a transparent window allowing the user to view the contents of compartment 108, an opaque panel designed to change colour once the fluid has been fully injected, or may be of some other design.

Injection device 300 also comprises sternal notch locator 304. Sternal notch locator 304 may aid a user in finding the appropriate location on a patient's sternum to position injection device 300, in order to facilitate maximum transfer of the fluid in compartment 108. In general, the desired injection location on the sternum can be located by palpating the deep notch at the top of the sternum, and measuring one finger width down from it on the centre line of the chest. Sternal notch locator 304 may assist a user in finding this location.

While the embodiment of FIGS. 5, 6, and 7 shows a locator device specifically configured for a patient's sternum, other locator devices may be configured for other locations, such as a patient's leg for access to the bone marrow of the tibia. A locator device may also be removably attachable to injection device 300, to allow different locators to be attached for use in different situations.

Figure 8:
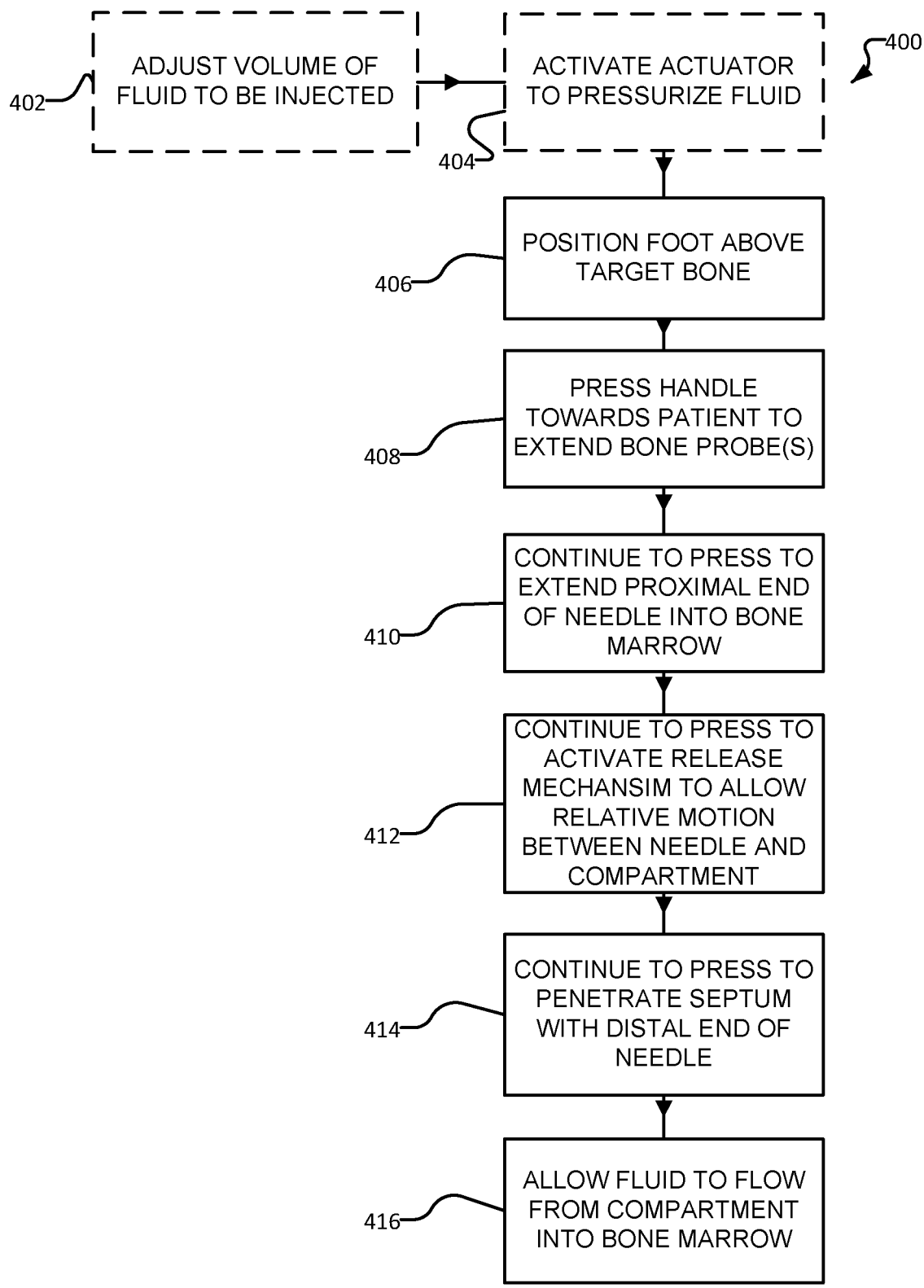
FIG. 8 is a flow diagram of the steps a user may take to operate an injection device, according to one embodiment of the invention.

FIG. 8 shows a process 400 which a user may perform in order to deploy one of the injection devices described above. Process 400 may also be used with alternative embodiments of the invention.

Process 400 begins in block 402 in which the user may adjust the amount of fluid to be injected.

In block 404, the user may trigger pressurization of fluid in the injection device (e.g. by removing a pin, compressing a spring, releasing a catch or the like). In some embodiments described above pressurization is triggered by removing actuation pin 104 to allow pressurization by spring 102.

In block 406, the user positions the foot of an injection device on the injection location above the target bone. The target bone may be any bone which provides access to the patient's bone marrow, for example the sternum, tibia, or femur.

In block 408, the user may then begin to press the handle of the injection device proximally towards the patient in order to extend the bone probe(s), which may penetrate the patient's skin and tissue and come to rest on the surface of the target bone.

In block 410, as the user continues to press the handle of the injection device, the stylet needle extends past the bone probe(s) to penetrate the target bone and come to rest in the patient's bone marrow.

In block 412, the depth limiter release mechanism is activated. This action also establishes a fluid connection between the pressurized contents of the compartment and the stylet needle in block 414.

In block 416, the user waits while the fluid escapes under pressure from the compartment so that it is injected into the patient's bone marrow.

For the purpose of illustration, it has been described that in some possible embodiments, injection devices 100 and/or 300 comprise compression spring 102. In some alternative embodiments, compression spring 102 may be replaced with any equivalent pressurizing mechanism, such as pressurized gas, one or more extension springs arranged to axially compress the compartment or the like.

For the purpose of illustration, it has been described that in some possible embodiments, injection devices 100 and/or 300 comprise actuation pin 104. In some alternative embodiments, actuation pin 104 is replaced with another actuating mechanism, such as a release button, trigger, or the like.

For the purpose of illustration, it has been described that in some possible embodiments, injection devices 100 and/or 300 comprise plunger 106 as part of compartment 108. In some alternative embodiments, plunger 106 may be incorporated into the compression mechanism or another component of injection devices 100 and/or 300. For example, compartment 108 may have a penetrable seal or membrane at its distal end which may be punctured by plunger 106, which is attached to the compression mechanism, when the compression mechanism is released.

For the purpose of illustration, it has been described that in some possible embodiments, injection devices 100 and/or 300 comprise a single-use device which comes pre-loaded with a set amount of the fluid to be injected. In some possible embodiments, compartment 108 may be removed and replaced with another sealed compartment prior to injection.

For the purpose of illustration, it has been described that in some embodiments, injection devices 100 and/or 300 comprise an indicator window 306 to indicate when the fluid has been fully injected into a patient. In some alternative embodiments, injection devices 100 and/or 300 comprise a second indicator window which indicates whether the fluid in compartment 108 has been contaminated or has leaked out prior to injection. This second indicator window may be a transparent window into the contents of compartment 108, an opaque panel which changes colour to indicate contamination or leakage, or may be of some other design.

This application is intended to cover any variations, uses, or adaptations of the invention using its general principles.

Further, this application is intended to cover such departures from the present disclosure as come within known or customary practice in the art to which this invention pertains and which fall within the limits of the appended claims. Accordingly, the scope of the claims should not be limited by the preferred embodiments set forth in the description, but should be given the broadest interpretation consistent with the description as a whole.

Where a component (e.g. needle, compartment, spring, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An intraosseous injector useful for injecting a fluid into a patient's bone marrow, the injector comprising:
   a housing;
   a container located within the housing;
   a hollow needle having proximal and distal ends, the needle slidable axially relative to the housing and having a proximal end projecting from a proximal end of the housing;
   a release mechanism comprising a bone probe needle and a release member movable between a first configuration in which the member blocks the needle from moving axially relative to the housing in a first direction that would move the proximal end of the needle toward the housing and a second configuration in which the member does not prevent the proximal end of the needle from moving in the first direction, the bone probe needle coupled to the release member such that the bone probe needle is configured to displace the release member to free the release member to move from the first configuration to the second configuration; and
   a valve comprising a septum configured to be penetrated by motion of the hollow needle in the first direction to establish fluid communication between an interior of the container and a bore of the hollow needle, wherein the septum is configured such that a force required to penetrate the septum and establish fluid communication is less than a force required to push the hollow needle into the patient's bone marrow to ensure the hollow needle stays at an appropriate depth in the bone marrow as the septum is penetrated,
   wherein the container is pressurized such that the fluid in the container is urged to flow through the hollow needle into the patient's bone marrow once the fluid communication between the interior of the container and the bore of the hollow needle is established when the septum is penetrated by the hollow needle.

2. An intraosseous injector according to claim 1 wherein the distal end of the needle is sharp and configured to penetrate the septum upon axial motion of the needle relative to the housing in the first direction.

3. An intraosseous injector according to claim 1, wherein the housing comprises a hand grip.

4. An intraosseous injector according to claim 1, comprising a tubular needle housing slidably mounted in the housing and biased to project in a proximal direction from the proximal end of the housing, the needle extending through a bore of the needle housing.

5. An intraosseous injector according to claim 4 comprising a foot on a proximal end of the needle housing.

6. An intraosseous injector according to claim 5 wherein the foot comprises indicia for aligning the foot with a target bone.

7. An intraosseous injector according to claim 6 wherein the indicia comprises a notch on an edge of the foot.

8. An intraosseous injector according to claim 1, wherein:
   a. the container is slidably movable relative to the housing in a second direction opposite to the first direction,
   b. the injector comprises a spring biasing the container to move in the second direction,
   c. the injector comprises a blocking member movable between a blocking position in which the container is held against moving in the second direction relative to the housing and a released position wherein the blocking member permits the container to move in the second direction, and
   d. motion of the needle in the first direction directly or indirectly moves the blocking member from the blocking position to the released position, thereby allowing the container to move in the second direction toward the needle.

9. An intraosseous injector according to claim 1, wherein the needle is attached to carriage that is slidably mounted in a bore of the housing and the injector comprises a one-way ratchet mechanism oriented to permit the carriage to move into the bore of the housing in the first direction.

10. An intraosseous injector according to claim 1, comprising a pressurization mechanism operable to pressurize the fluid within the container.

11. An intraosseous injector according to claim 10 wherein the pressurization mechanism comprises a supply of a pressurized gas.

12. An intraosseous injector according to claim 10 wherein the pressurization mechanism comprises a plunger and a spring arranged drive the plunger to pressurize the fluid in the container.

13. An intraosseous injector according to claim 12 wherein the plunger forms one wall of the container.

14. An intraosseous injector according to claim 13 comprising a stop adjustable to selectively limit a travel of the plunger.

15. An intraosseous injector according to claim 14 wherein the stop comprises a removable pin.

16. An intraosseous injector according to claim 15 comprising a visible indicator connected to move in response to motion of the plunger, a position of the visible indicator indicative of an amount of fluid that has been dispensed from the container.

17. An intraosseous injector according to claim 1 comprising an indicator showing a proportion of the fluid from the container that has been injected.

18. An intraosseous injector according to claim 17 wherein the indicator comprises a window in the housing through which the container is visible.

19. An intraosseous injector according to claim 18 wherein a wall of the container is translucent or transparent.

20. An intraosseous injector according to claim 1, wherein the container contains a fluid comprising a drug.

21. An intraosseous injector according to claim 20 wherein the drug is selected from the group consisting of epinephrine, antidotes, heart medications, and medications to treat one or more of: blood loss, infections, hypotension, organophosphate poisoning, burns, trauma, pain and seizures.

22. An intraosseous injector according to claim 1, wherein the proximal end of the needle comprises one or more fluid ports extending into the bore of the needle through a side wall of the needle.

23. An intraosseous injector according to claim 22 wherein the proximal end of the needle comprises a solid pointed tip.

24. An intraosseous injector according to claim 1, wherein the proximal end of the needle is enlarged in diameter relative to a portion of the needle adjacent to the proximal end of the needle.

25. An intraosseous injector according to claim 1, wherein the release member comprises a split ring coupled to the housing and a sliding block coupled to the bone probe, the sliding block located in a gap between ends of the split ring and displaceable out of the gap by a force applied to the bone probe.

26. An intraosseous injector according to claim 1, wherein the bone probe comprises a plurality of bone probe needles.

27. An intraosseous injector according to claim 26 wherein the bone probe needles extend parallel to and surround the needle.

28. An intraosseous injector according to claim 1, wherein the container has a capacity of at least 3 ml of the fluid.

29. An intraosseous injector according to claim 1 wherein the container comprises a frangible ampule.

30. An intraosseous injector according to claim 1, further comprising a carrier and a trigger tab configured to support the container, wherein the trigger tab is operable to hold the container against moving proximally inside the housing.

* * * * *